United States Patent [19]
Hauck et al.
[11] 4,279,902
[45] Jul. 21, 1981

[54] ANTI-ARRHYTHMIA AGENTS

[75] Inventors: Frederic P. Hauck, Bridgewater; Glenn A. Jacobs, Princeton, both of N.J.

[73] Assignee: E. R. Squibb & Sons, Inc., Princeton, N.J.

[21] Appl. No.: 175,626

[22] Filed: Aug. 6, 1980

[51] Int. Cl.³ .................... A61K 31/34; A61K 31/35; A61K 31/335; C07D 307/24

[52] U.S. Cl. ................................424/246; 260/326.25; 260/326.36; 260/330; 260/340.6; 260/340.9 R; 260/345.7 R; 260/345.8 R; 260/345.9 R; 260/347.3; 260/347.4; 424/248.54; 424/250; 424/251; 424/267; 424/270; 424/273 R; 424/274; 424/275; 424/278; 424/283; 424/285; 544/3; 544/54; 544/58.4; 544/63

[58] Field of Search ..................... 260/326.25, 326.36, 260/330, 340.6, 345.7 R, 345.8 R, 347.3, 347.4; 544/3, 58.4, 54, 63, 87, 96, 148, 149, 152, 238, 296, 335, 357, 374; 546/187, 207, 214; 548/200, 214, 215, 240, 300, 356; 424/246, 248.54, 250, 251, 267, 270, 273 R, 274, 275, 278, 283, 285

[56] References Cited

PUBLICATIONS

Mukai et al., Chemical Abstracts, vol. 80 (1974) 97,333y.

*Primary Examiner*—Richard Raymond
*Attorney, Agent, or Firm*—Lawrence S. Levinson; Burton Rodney

[57] ABSTRACT

Acetamide derivatives are provided having the structure

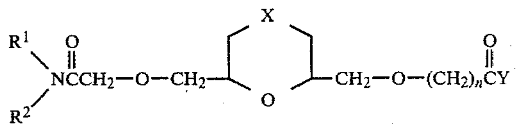

wherein X is a single bond, $-CH_2-$ or $-O-$, $R^1$ and $R^2$ may be the same or different and are lower alkyl, phenyl-lower alkoxy-lower alkyl, lower alkenyl, phenyl-lower alkyl or lower alkoxy, or

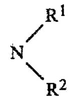

may be taken together to form a 5- to 7-membered heterocyclic ring optionally containing one other hetero atom, such as nitrogen, sulfur or oxygen; Y is hydroxyl, OR wherein R is lower alkyl, lower alkenyl or lower alkanoyl, or

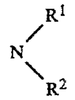

wherein $R^1$ and $R^2$, and $R^1$ and $R^2$ taken together with the nitrogen to which they are attached are as defined above, and n is 1 to 6.

These compounds are useful as anti-arrhythmia agents and have been found to be effective in the treatment of acute myocardial infarction.

11 Claims, No Drawings

ANTI-ARRHYTHMIA AGENTS

DESCRIPTION OF THE INVENTION

The present invention relates to compounds which are useful in treating arrhythmia and acute myocardial infarction and have the formula

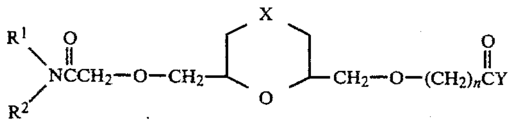

I wherein X is $-(CH_2)_m-$ or oxygen;

$R^1$ and $R^2$ are the same or different and are lower alkyl, lower alkenyl, phenyl-lower alkyl, lower alkoxy or phenyl-lower alkoxy-lower alkyl, or $R^1$ and $R^2$ taken together with the nitrogen to which they are attached may form a 5-, 6- or 7-membered heterocyclic ring optionally containing one other hetero atom, such as nitogen, sulfur or oxygen;

Y is hydroxyl, OR wherein R is lower alkyl, lower alkenyl, or lower alkanoyl, or

wherein $R^1$, $R^2$, and $R^1$ and $R^2$ taken together with the nitrogen to which they are attached, are as defined above; and n is an integer from 1 to 6, and m is 0 or 1.

Thus, the nucleus

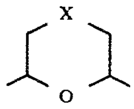

includes

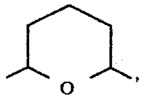,

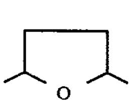

or

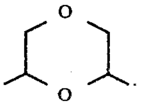.

The term "lower alkyl" as employed herein includes both straight and branched chain radicals of up to 8 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl and the like as well as such groups including a halo-substituent, such as F, Br, Cl or I or $CF_3$ or a phenyl substituent.

The term "lower alkenyl" as employed herein includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "lower alkanoyl" refers to any of the above lower alkyl groups attached to a carbonyl group

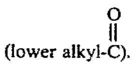

The "lower alkoxy" refers to any of the above lower alkyl groups attached to an oxygen (lower alkyl-O).

As indicated, the group

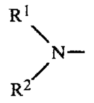

may form a heterocyclic radical containing in addition to nitrogen, one other hetero atom, such as nitrogen, oxygen or sulfur, and may contain up to 6 carbons.

The heterocyclic radicals may include one to three substituents including lower alkoxy or lower alkyl as defined herein; trihalomethoxy, such as trifluoromethoxy; trihalomethylmercapto, such as trifluoromethylmercapto; N,N-dialkylsulfamoyl groups, such as N, N-dimethylsulfamoyl; lower alkanoyl groups

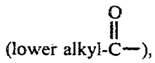

such as acetyl, propionyl, and the like; hydroxy; hydroxy-lower alkyl, such as hydroxymethyl, 2-hydroxyethyl, or the like; hydroxy-lower alkoxy-lower alkyl, such as 2-(2-hydroxyethoxy)ethyl, or the like; lower alkanoyloxy; alkanoyloxy-lower alkyl (up to about 14 carbons in the alkanoyl group), such as 2-heptanoyloxyethyl; carbo-lower alkoxy, such as carbomethoxy, carboethoxy, carbopropoxy, or the like; or 2-(alkanoyloxy-lower alkoxy)lower alkyl (with up to about 14 carbons in the alkanoyl group), such as 2-(decanoyloxyethoxy)-ethyl, or the like.

Illustrative of the heterocyclic radicals represented by

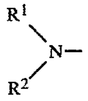

are the following: piperidino; (lower alkyl)piperidino [e.g., 2-, 3-, or 4-(lower alkyl)piperidino, such as 2-(ethyl)piperidino] or di(lower alkyl)piperidino [e.g., 2,4-, 2,5- or 3,5-di(lower alkyl)piperidino such as 2,4-dimethylpiperidino or 2,5-di-t-butyl piperidino]; (lower alkoxy)-piperidino [e.g., 2-methoxypiperidino or 3-methoxypiperidino]; hydroxypiperidino 8 e.g., 3-hydroxy- or 4-hydroxypiperidino]; aminomethylpiperidino [e.g., 4-aminomethylpiperidino]; pyrrolidino; (lower alkyl)pyrrolidino [e.g., 3-methylpyrrolidino]; di(lower alkyl)pyrrolidino [e.g., 3,4-dimethylpyrrolidino]; (lower alkoxy)pyrrolidino [e.g., 2-methoxypyrrolidino]; morpholino; (lower alkyl)morpholino [e.g., 3-methylmorpholino]; di(lower alkyl)morpholino [e.g., 3,5-dimethylmorpholino]; (lower alkoxy)morpholino [e.g., 2-methoxymorpholino]; thiamorpholino; (lower alkyl)thiamorpholino [e.g., 3-methylthiamorpholino]; di(lower alkyl)thiamorpholino [e.g., 3,5-dimethylthiamorpholino]; (lower alkoxy)thiamorpholino [e.g., 3-methoxythiamorpholino]; piperazino; (lower alkyl)piperazino [e.g., $N^4$-methylpiperazino]; di(lower alkyl)piperazino [e.g., 2,5-dimethylpiperazino or 2,6-dimethylpiperazino]; (lower alkoxy)piperazino [e.g., 2-methoxypiperazino]; (hydroxylower alkyl)piperazino [e.g., $N^4$-(2-hydroxyethyl)-piperazino]; (alkanoyloxy-lower alkyl)piperazino wherein the alkanoyloxy group has up to 14 carbons [e.g., $N^4$-(2-heptanoyloxyethyl)-piperazino or $N^4$-(2-dodecanoyloxyethyl)piperazino]; (hydroxylower alkoxy-lower alkyl)piperazino [e.g., (hydroxymethoxy-methyl)piperazino]; (carbo-lower alkoxy)piperazino [e.g., $N^4$-(carbomethoxy-, carboethoxy-, or carbopropoxy)piperazino]; homopiperazino; or $N^4$-(hydroxy-lower alkyl)homopiperazino [e.g., $N^4$-(2-hydroxyethyl)homopiperazino].

The compounds of this invention where Y is OH form basic salts with various inorganic bases which are also within the scope of the invention. Such salts include ammonium salts, alkali metal salts like sodium and potassium salts (which are preferred), alkaline earth metal salts like the calcium and magnesium salts.

Preferred are those compounds of formula I wherein X is $(CH_2)_m$ which represents a single bond, $R^1$ and $R^2$ are each lower alkyl, such as propyl, n is 1 and Y is di(lower alkyl)amino, such as dipropylamino or carboxyl.

The compounds of formula I may be prepared according to the following reaction sequence.

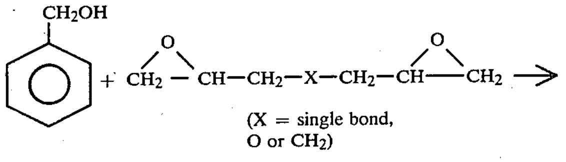

II III

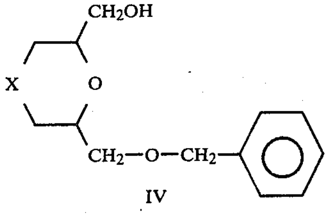

IV

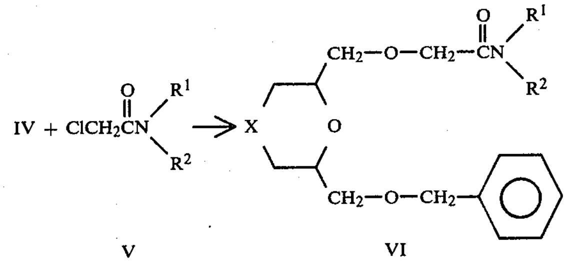

V VI

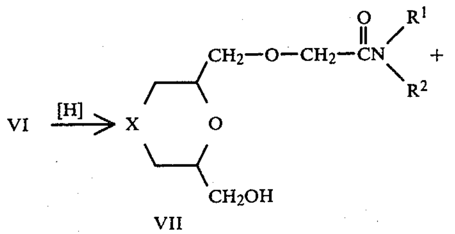

VII

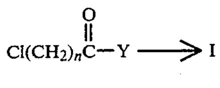

VIII

In carrying out the above reactions, the benzyl alcohol II is reacted with the diepoxy compound III in the presence of sodium in a molar ration of II:III of within the range of from about 0.5:1 to about 4:1, and preferably from about 1:1 to about 2:1, at a temperature of within the range of from about 80° to about 140° C., and preferably from about 90° to about 120° C., for a period of from about 0.5 to about 12 hours or more. The benzyloxymethyl compound IV is then reacted with amide V in the presence of an inert solvent, such as dimethylsulfoxide and a hydrogenating agent, such as sodium hydride to form the compound of structure VI. The above reaction may be carried out at ambient temperature, employing a molar ratio of IV:V of within the range of from about 0.5:1 to about 4:1, and preferably from about 1:1 to about 2:1, for a period of 15 minutes to up to 4 hours or more.

The formula VI compound is then reduced to the formula VII compound in the presence of a hydrogenation catalyst, such as palladium on charcoal or platinum oxide.

The compound VII is then reacted with compound VIII (molar ratio of VII:VIII of within the range of from about 0.5:1 to about 4:1, and preferably from about 1:1 to about 2:1), in the presence of an inert solvent, such as dimethylsulfoxide, dioxane, glyme or diglyme, and sodium hydride to form the formula I compounds of the invention.

Alternatively, compounds of formula I in the form of monoamide monoacids, that is, wherein Y is OH, may be prepared by reacting the diepoxide III with allyl alcohol IX in the presence of sodium to form a compound of the structure X

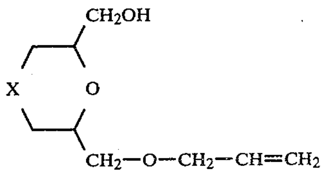

X

The above reaction is carried out employing a mole ratio of III:IX of within the range of from about 0.5:1 to about 4:1, and preferably from about 1:1 to about 2:1, at a temperature within the range of from about 60° to about 100° C. for a period of from about 15 minutes to about 4 hours.

Compound X (in place of IV) is then reacted with the amide V in a manner described hereinbefore with respect to the preparation of amide VI to form the compound XI

XI

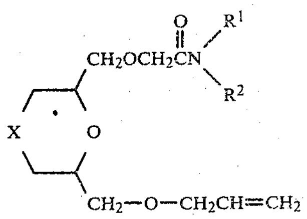

which is then oxidized to the corresponding acid Ia, for example, by reaction with potassium permanganate in cold acetone Ia

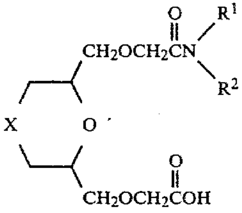

In yet another alternative method, the compounds of formula XI may be reacted with m-chloro benzoic acid to form a compound of the structure

XII

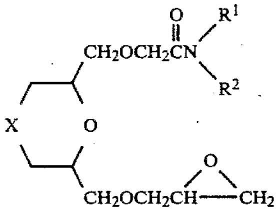

which is then oxidized to the corresponding mono acid Ia by reaction with lead tetraacetate.

Mono amide mono acids Ia may also be prepared by reacting diepoxide III with solketal in the presence of sodium to form a compound of the structure XIII

XIII

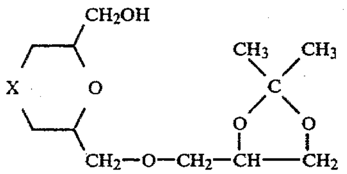

which is then converted to the corresponding monoamide XIV by reaction with amide V in the presence of a hydrogenating agent as described above for the preparation of amide VI,

XIV

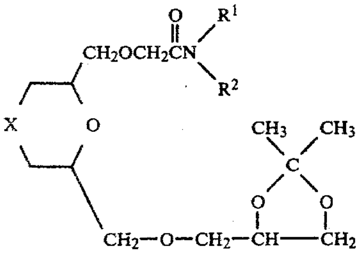

which is then oxidized to the corresponding acid Ia in a manner similar to that described hereinbefore with respect to the oxidation of XI and XII.

In addition, in accordance with the present invention, there is provided a number of novel intermediates, namely compounds of the formulae

IV

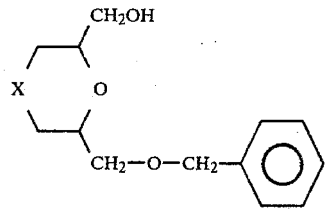

,

X

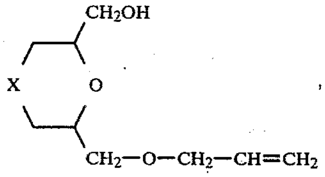

,

XIII

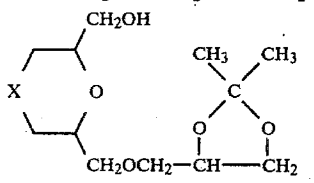

compounds of the formulae

VI

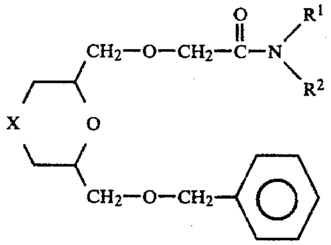

,

XI

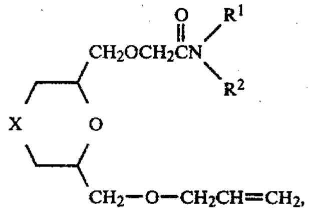

XIV

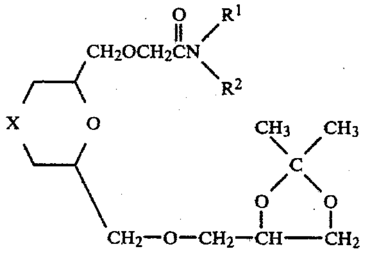

and compounds of the formula VIII

VIII

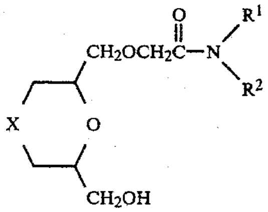

In the above formulae, R, $R^1$, $R^2$ and

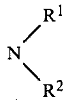

are as defined hereinbefore with respect to the compounds of formula I.

The compounds of formula I have antiarrhythmic activity as indicated by the Harris coronary-ligated dog test described by A. S. Harris in *Circulation*, 1:1318–1328, 1950. and are useful in the treatment of arrhythmia in mammalian species, for example, rats and dogs. In addition, the compounds of formula I have been found to be effective in treating acute myocardial infarction in anesthetized dog model as indicated by the test described by A. S. Harris, supra.

A compound of formula I as well as its physiologically acceptable salts may be compounded according to pharmaceutical practice in oral or parenteral dosage forms, such as tablets, capsules, elixirs, injectables or powders for administration of about 100 mg to 400 mg per day, preferably 125 mg to 175 mg per day, in 2 to 4 divided doses.

The following Examples represent preferred embodiments of the present invention. Unless otherwise indicated, all temperatures are expressed in degrees Centigrade.

EXAMPLE 1

2,2'-[Tetrahydrofuran-2,5-diylbis(methoxy)]-bis-[N,N-dipropylacetamide]

A.

Tetrahydro-5-[(phenylmethoxy)methyl]-2-furanmethanol 100 ml of benzyl alcohol (0.97 mol) is cooled to 5° in an ice-bath and under a nitrogen atmosphere. 0.32 g of sodium (0.0139 mole; washed with hexane to remove the mineral oil) is slowly added to the rapidly stirred benzyl alcohol. The addition of the sodium is made at such a rate that the temperature remains below 20°. After the addition of the sodium has been completed the mixture is allowed to stir for ½ hour and slowly warmed to room temperature. Slowly, and with stirring 20 g of 1,5-hexadiene diepoxide (0.175 mole) is added to the mixture. After the addition of the diepoxide has been completed, the reaction mixture is heated at 150° for 16 hours. The mixture is then cooled to room temperature and with stirring is poured into 350 ml of water. The aqueous mixture is extracted with 2×250 ml portions of chloroform, the $CHCl_3$ extracts are combined and dried over anhydrous sodium sulfate. The $CHCl_3$ is removed in vacuo and the colorless oil vacuum distilled through a 10 cm vigreux distilling column. The fraction distilling at 151°–155° @0.5 mm is collected yielding 18.52 g (48%) of the above compound.

B.

N,N-Dipropyl-2-[[tetrahydro-5-[(phenylmethoxy)methyl]-2-furanyl]methoxy]acetamide A mixture of 4.44 g of tetrahydro-5-[(phenylmethoxy)methyl]-2-furanmethanol (0.02 mole) and 3.55 g of 2-chloro-N,N-dipropylacetamide (0.02 mole) is dissolved in 125 ml of dry dimethyl sulfoxide and the mixture stirred at room temperature under nitrogen. Slowly, 0.50 g of sodium hydride (0.02 mole) is added to the dimethyl sulfoxide mixture and the reaction allowed to stir at ambient temperature (23°). After stirring for 10 minutes an exothermic reaction begins to take place and an ice-bath is used to maintain the reaction temperature below 30°. After stirring for 1 hour, the ice-bath is removed and the reaction allowed to stir at room temperature for 18 hours. The excess NaH is destroyed by adding 5 ml of methanol and the entire reaction mixture is then poured into 400 ml of water. The product is extracted with 3×125 ml portions of chloroform. The $CHCl_3$ extracts are combined and washed with 4×300 ml portions of water. The $CHCl_3$ is then removed in vacuo yielding a pale yellow oil which is vacuum distilled and the fraction distilling at 210°–225° @0.5 mm is collected yielding 5.2 g (72%) of the above compound.

C.

N,N-Dipropyl-2-[[tetrahydro-5-(hydroxymethyl)-2-furanyl]methoxy]acetamide

To a solution of 10.9 g of N,N-dipropyl-2-[[tetrahydro-5-[(phenylmethoxy)methyl]-2-furanyl]methoxy]acetamide (0.03 mole) in 125 ml of glacial acetic acid is added 2.5 g of 10% palladium on carbon. The mixture is hydrogenated at 55 psi over a period of 18 hours (debenzylation reaction taking up 98% of the calculated theory). The mixture is removed and the Pd/C filtered through a pad of "celite" filter aid. The acetic acid is then removed in vacuo yielding a pale yellow oil. The resulting oil is dissolved in 100 ml of ethanol and evaporated. The oil is then redissolved in ethanol and again evaporated in vacuo. The oil is then taken up in 200 ml of chloroform and washed with 100 ml of saturated $NaHCO_3$ solution, 150 ml of water and finally with 200 ml of saturated NaCl solution. The $CHCl_3$ layer is separated, dried over anhydrous $Na_2SO_4$ and then the $CHCl_3$ is removed in vacuo yielding 7.6 g of crude product whih is vacuum distilled and the fraction distilling at 180°–183° @ 0.4 mm is collected yielding 7.1 g (87%) of the above compound.

D.

2,2'-[Tetrahydrofuran-2,5-diylbis(methoxy)]bis[N,N-dipropylacetamide]

A mixture of 4.08 g of N,N-dipropyl-2-[[tetrahydro-5-(hydroxymethyl)-2-furanyl]methoxy]acetamide (0.0149 mole) and 2.65 g of 2-chloro-N,N-dipropylacetamide (0.0149 mole) is dissolved in 125 ml of dry dimethyl sulfoxide and the mixture stirred at room temperature under nitrogen. Slowly, 0.72 g of sodium hydride (0.015 mole; 50% oil dispersion) is added to the dimethyl sulfoxide mixture and the reaction allowed to stir at ambient temperature (22°). After stirring for 10 minutes an exothermic reaction begins to take place and an ice-bath is used to maintain the reaction temperature below 30°. After stirring for ½ hour, the ice-bath is removed and the reaction allowed to stir at room temperature for 18 hours. The excess NaH is destroyed by adding 5 ml of methanol and the entire reaction mixture is then poured into 400 ml of water. The product is extracted with 3×125 ml portions of chloroform. The $CHCl_3$ extracts are combined and washed with 4×300 ml portions of water. The $CHCl_3$ layer is separated and dried over anhydrous $Na_2SO_4$ overnight. The $CHCl_3$ is removed in vacuo yielding a yellow oil which is vacuum distilled and the fraction distilling at 227°–230° @ 0.25 mm is collected. A second redistillation yields 2.86 g (47%) of the title product as a slightly darker yellow oil, b.p. 228°–230° @ 0.25 mm.

EXAMPLE 2

2,2'-[(1,4-Dioxane-2,6-diyl)bis(methyleneoxy)]bis[N,N-dipropylacetamide]

A. 6-[(Phenylmethoxy)methyl]-1,4-dioxane-2-methanol 108 g of benzyl alcohol (1.0 mole) is stirred under a nitrogen atmosphere at room temperature and 0.4 g of sodium is added to the mixture and stirring continued for 2-½ hours. Then 13.1 g of 2,2'-(oxybismethylene)-bisoxirane (0.1 mole) is added and the mixture then heated to reflux for 18 hours. The mixture is then cooled to room temperature and with stirring is poured into 350 ml of water. The aqueous mixture is extracted with 2×200 ml portions of chloroform, the $CHCl_3$ extracts are combined and dried over anhydrous sodium sulfate. The $CHCl_3$ is removed in vacuo and the resulting yellow oil then vacuum distilled through a 10 cm vigreux column. The fraction distilling at 150°-154° @0.4 mm is collected yielding 4.8 g (20%) of the above compound.

B.

2-[[6-[(Phenylmethoxy)methyl]-1,4-dioxolan-2-yl]methoxy]-N,N-dipropylacetamide

Following the procedure of Example 1B, except substituting 6-[(phenylmethoxy)methyl]-1,3-dioxane-2-methanol for tetrahydro-5-[(phenylmethoxy)methyl]-2-furanmethanol, the above compound is obtained.

C.

2-[[6-(Hydroxymethyl)-1,4-dioxolan-2-yl]methoxy]-N,N-dipropylacetamide

Folowing the procedure of Example 1C, except substituting 2-[[6-[(phenylmethoxy)methyl]-1,4-dioxolan-2-yl]methoxy]-N,N-dipropylacetamide for N,N-dipropyl-2-[[tetrahydro-5-[(phenylmethoxy)methyl]-2-furanyl]methoxy]acetamide, the above compound is obtained.

D.

2,2'-[(1,4-Dioxane-2,6-diyl)bis(methyleneoxy)]bis[N,N-dipropylacetamide]

Following the procedure of Example 1D, except substituting 2-[[6-(hydroxymethyl)-1,4-dioxolan-2-yl]methoxy]-N,N-dipropylacetamide for N,N-dipropyl-2-[[tetrahydro-5-(hydroxymethyl)-2-furanyl]methoxy]acetamide, the title product is obtained.

EXAMPLE 3

[[6-[[2-(Dipropylamino)-2-oxoethoxy]methyl]-1,4-dioxan-2-yl]methoxy]acetic acid

A. 2,2'-(Oxybismethylene)bisoxirane 28.54 g of allyl glycidyl ether (0.15 mole) (Aldrich) is dissolved in 1000 ml of methylene chloride and cooled to 0° in an ice bath. In one single addition 51.75 g of m-chloroperoxybenzoic acid (1.05 equiv. @ 85% tech) (Aldrich) is added and the reaction stirred rapidly at 0° for 4 hours. The reaction is allowed to slowly warm to room temperature and stirred overnight. The precipitated m-chlorobenzoic acid is removed via filtration and washed with 50 ml of cold $CH_2Cl_2$. The $CH_2Cl_2$ solution is then washed with 2×200 ml of saturated potassium carbonate solution and dried over $Na_2SO_4$. The $CH_2Cl_2$ is removed in vacuo yielding 30.6 g (94%) of 2,2'-(oxybismethylene)bisoxirane as a colorless liquid.

B. 6-[(2-Propenyloxy)methyl]-1,4-dioxane-2-methanol 136 ml of allyl alcohol (2.0 mole, Aldrich) is stirred under nitrogen at room temperature and 0.25 g of sodium is added to the mixture and stirring continued for 2.5 hours. Then 13.1 g of 2,2'-(oxybismethylene)bisoxirane (0.1 mole) is added and the mixture then heated at reflux for 18 hours. The mixture is then cooled to room temperature and with stirring is poured into 350 ml of water. The aqueous mixture is extracted with 2×200 ml portions of chloroform, the $CHCl_3$ extracts are combined and dried over anhydrous sodium sulfate. The $CHCl_3$ is removed in vacuo and the resulting yellow oil then vacuum distilled through a 10 cm vigreux column. The fraction distilling at 120°-123° @ 0.4 mm is collected yielding 3.2 g (18%) of the above compound.

C.

2-[[6-[(2-Propenyloxy)methyl]-1,4-dioxan-2-yl]methoxy]-N,N-dipropylacetamide

Following the procedure of Example 1B except substituting 6-[(2-propenyloxy)methyl]-1,4-dioxane-2-methanol for N,N-dipropyl-2-[[tetrahydro-5-[(phenylmethoxy)methyl]-2-furanyl]methoxy]acetamide, the above monoamide is obtained.

D.

[[6-[[2-(Dipropylamino)-2-oxoethoxy]methyl]-1,4-dioxan-2-yl]methoxy]acetic acid

A solution of 8.23 g (0.025 mole) of 2-[[6-[(2-propenyloxy)methyl]-1,4-dioxan-2-yl]methoxy]-N,N-dipropylacetamide in 350 ml of dry acetone is stirred at −20°, treated with 12.0 ml (0.12 mole) of piperidine and 9.53 g of potassium permanganate (0.06 mole). The mixture is stirred for 30 minutes, and treated below −20° with 2 ml of acetic acid in 25 ml of acetone. After 4 hours at −20°, 250 ml of chloroform is added (−20°), followed by careful addition of 30 ml of concentrated hydrochloric acid in 150 ml of water and 14 g of sodium bisulfite in 100 ml of water. Extraction with chloroform, evaporation and vacuum distillation of the resulting yellow oil, yields 4.3 g (54%), b.p. 131°-135° @ 0.1 mm, of the above compound.

EXAMPLE 4

[[5-[[2-(Dipropylamino)-2-oxoethoxy]methyl]tetrahydro-2-furanyl]methoxy]acetic acid

A.

Tetrahydro-5-[(2-propenyloxy)methyl]-2-furanmethanol 100 ml of allyl alcohol (1.47 mole, Aldrich) is cooled to 5° in an ice-bath and under a nitrogen atmosphere 0.3 g of sodium (0.013 mole, washed with hexane to remove the mineral oil) is slowly added to the rapidly stirred mixture. The addition of the sodium is made at such a rate that the temperature remains below 20°. After the addition of the sodium has been completed, the mixture is allowed to stir for ½ hour and slowly warmed to room temperature. Slowly, with stirring 15.0 g of 1,5-hexadiene diepoxide (0.131 mole) is added to the mixture. After the addition of the diepoxide has been completed, the reaction mixture is heated at reflux for 16 hours. The mixture is then cooled to room temperature and with stirring is poured into 350 ml of water. The aqueous mixture is extracted with 2×200 ml portions of chloroform, the $CHCl_3$ extracts are combined and dried over anhydrous sodium sulfate. The $CHCl_3$ is removed in vacuo and the resulting yellow oil then vacuum distilled through a 10 cm vigreux distilling column. The fraction distilling at 108°–110° @ 0.5 mm is collected yielding 14.65 g (65%) of the above compound.

B.

N,N-Dipropyl-2-[[tetrahydro-5-[(2-propenyloxy)methyl]-2-furanyl]methoxy]acetamide A mixture of 6.89 g of tetrahydro-5-[(2-propenyloxy)-methyl]-2-furanmethanol (0.04 mole) and 7.12 g of 2-chloro-N,N-dipropylacetamide (0.02 mole) are dissolved in 200 ml of dry dimethyl sulfoxide and the mixture stirred at room temperature under nitrogen. Slowly, 0.50 g of sodium hydride (0.02 mole) is added to the dimethyl sulfoxide mixture and the reaction allowed to stir at ambient temperature (23°). After stirring for 10 minutes an exothermic reaction begins to take place and an ice-bath is used to maintain the reaction temperature below 30°. After stirring for 1 hour, the ice-bath is removed and the reaction allowed to stir at room temperature for 18 hours. The excess NaH is destroyed by adding 5 ml of methanol and the entire reaction mixture is then poured into 400 ml of water. The product is extracted with 3×125 ml portions of chloroform. The $CHCl_3$ extracts are combined and washed with 4×300 ml portions of water. The $CHCl_3$ layer is separated and dried over anhydrous $Na_2SO_4$ overnight. The $CHCl_3$ is removed in vacuo yielding a pale yellow oil which is vacuum distilled and the fraction distilling at 185°–188° @ 0.5 mm is collected yielding 8.84 g (70%) of the above compound.

C.

N,N-Dipropyl-2-[[tetrahydro-5-[(oxiranylmethoxy)methyl]-2-furanyl]methoxy]acetamide 5.0 g of N,N-dipropyl-2-[[tetrahydro-5-[(2-propenyloxy)methyl]-2-furanyl]methoxy]acetamide (0.016 mole) is dissolved in 300 ml of methylene chloride and 3.20 g of m-chlorobenzoic acid (1 equivalent @ 85% tech) is added at room temperature. The mixture is then stirred at 30° for 72 hours under nitrogen. The precipitated m-chlorobenzoic acid is removed via filtration. The methylene chloride mixture is then washed with 2×200 ml portions of saturated potassium carbonate solution and dried over anhydrous sodium sulfate. The methylene chloride is removed in vacuo yielding 4.86 g (92%) of the above compound as a pale yellow liquid.

D.

[[6-[[2-(Dipropylamino)-2-oxoethoxy]methyl]-1,4-dioxan-2-yl]methoxy]acetic acid

Following the procedure of Example 3D, except substituting N,N-dipropyl-2-[[tetrahydro-5-[(oxiranylmethoxy)methyl]-2-furanyl]methoxy]acetamide for N,N-dipropyl-2-[[tetrahydro-S-[(oxiranylmethoxy)methyl]-2-furanyl]methoxy]acetamide, the title product is obtained.

EXAMPLE 5

[[6-[[2-(Dipropylamino)-2-oxoethoxy]methyl]-tetrahydro-2H-pyran-2-yl]methoxy]acetic acid A. 1,6-Heptadiene diepoxide A mixture of 14.43 g of 1,6-heptadiene (0.15 mole) (Columbia organic Chemicals) in 400 ml of dichloromethane is cooled to 0° in an ice bath. In one single addition 62.6 g of m-chloroperoxybenzoic acid (2.1 equiv. @ 85% tech., Aldrich) is added and the reaction stirred rapidly at 0° for 4 hours. The reaction is allowed to slowly warm to room temperature and stir overnight. The precipitated m-chlorobenzoic acid is removed via filtration and washed with 100 ml of cold methylene chloride. The methylene chloride solution is washed with 2×200 ml portions of saturated potassium carbonate solution and dried over anhydrous $Na_2SO_4$. The $CH_2Cl_2$ is removed in vacuo yielding 14.46 g (73%) of 1,6-heptadiene diepoxide as a colorless liquid.

B.

6-[[(2,2-Dimethyl-1,3-dioxolan-4-yl)methoxy]methyl]-tetrahydro-2H-pyran-2-methanol 125 ml of solketal (1 mole) (Aldrich) is stirred at room temperature under a nitrogen atmosphere and 0.3 g of sodium is added. The mixture is then stirred until all of the sodium has reacted and dissolved (1 hour). Then 10.0 g of 1,6-heptadiene diepoxide (0.078 mole) is added to the mixture and stirring at room temperature continued for one hour. The reaction is then heated at reflux for 18 hours. The mixture is cooled to room temperature and is poured into 350 ml of water. The aqueous mixture is extracted with 2×200 ml portions of chloroform, the $CHCl_3$ extracts are combined and dried over anhydrous sodium sulfate. The $CHCl_3$ is removed in vacuo and the dark brown oil then vacuum distilled through a 10 cm vigreux column. The fraction distilling at 152°–156° @0.5 mm is collected yielding 17.18 g (85%) of the above compound.

C.

[[6-[[(2,2-Dimethyl-1,3-dioxolan-4-yl)methoxy]methyl]-tetrahydro-2H-pyran-2-yl]methoxy]-N,N-dipropylacetamide Following the procedure of Example 4B but substituting 6-[[(2,2-dimethyl-1,3-dioxolan-4-yl)methoxy]methyl]tetrahydro-2H-pyran-2-methanol for tetrahydro-5-[(2-propenyloxy)methyl]-2-furanmethanol, the above compound is obtained.

D.

[[6-[[2-(Dipropylamino)-2-oxoethoxy]methyl]tetrahydro-2H-pyran-2-yl]methoxy]acetic acid Following the procedure of Example 3D, except substituting [[6-[[(2,2-dimethyl-1,3-dioxolan-4-yl)methoxy]methyl]tetrahydro-2H-pyran-2-yl]methoxy]-N,N-dipropylacetamide for 2-[[6-[(2-propenyloxy)methyl]-1,4-dioxan-2-yl]methoxy]-N,N-dipropylacetamide, the title product is obtained.

EXAMPLE 6

[[5-[[2-(Dipropylamino)-2-oxoethoxy]methyl]-tetrahydro-2-furanyl]methoxy]acetic acid A. 1,5-Hexadiene diepoxide A mixture of 12.32 g of 1,5-hexadiene (0.15 mole) (Aldrich) in 400 ml of methylene chloride is cooled to 0° in an ice bath and the reaction flask equipped with a dry-ice/acetone condenser and an air stirrer. In one single addition 62.6 g of m-chloroperbenzoic acid (2.1 equiv. @ 85% tech, Aldrich) is added and the reaction stirred rapidly at 0° for 4 hours. The reaction is allowed to slowly warm to room temperature and stir overnight. The precipitated m-chlorobenzoic acid is removed via filtration and washed with 100 ml of cold methylene chloride. The $CH_2Cl_2$ mixture is then washed with two 200 ml portions of saturated potassium carbonate solution and dried over anhydrous $Na_2SO_4$. The $CH_2Cl_2$ is removed in vacuo yielding 15.4 g (90%) of 1,5-hexadiene diepoxide as a colorless liquid.

B.

5-[[(2,2-Dimethyl-1,3-dioxolan-4-yl)-methoxy]methyl]-tetrahydro-2-furanmethanol 46.3 g of 2,2-dimethyl-1,3-dioxolane-4-methanol (0.35 mol) (Aldrich) is cooled to 0° in an ice bath and under a nitrogen atmosphere 2.1 g of sodium hydride (0.088 mol) (washed with hexane to remove the mineral oil) is slowly added to the rapidly stirred mixture. The addition of the sodium hydride is made at such a rate that the temperature remains below 20°. After the addition of the NaH has been completed the mixture is allowed to stir for ½ hour and slowly warmed to room temperature. Slowly, and with stirring 10.0 g of 1,5-hexadiene diepoxide (0.088 mol) is added to the mixture. After the addition of the diepoxide has been completed the reaction mixture is heated at reflux for 16 hours. The mixture is then cooled to room temperature and with stirring is poured into 350 ml of water. The aqueous mixture is extracted with two 200 ml portions of chloroform, the $CHCl_3$ extracts are combined and dried over anhydrous sodium sulfate. The $CHCl_3$ is removed in vacuo and the dark brown residue then vacuum distilled through a 10 cm vigreux distilling column. The fraction boiling at 135°-137° @ 0.3 mm is collected yielding 12.6 g (58%) of the above compound.

C.

2-[[5-[[(2,2-Dimethyl-1,3-dioxolan-4-yl)-methoxy]methyl]tetrahydro-2-furanyl]-methoxy]-N,N-dipropylacetamide A mixture of 4.93 g of 5-[[(2,2-dimethyl-1,3-dioxolan-4-yl)methoxy]methyl]tetrahydro-2-furan-methanol (0.02 mole) and 3.55 g of 2-chloro-N,N-dipropylacetamide (0.02 mole) are dissolved in 125 ml of dry dimethyl sulfoxide and the mixture stirred at room temperature under nitrogen. Slowly 0.50 g of sodium hydride (0.02 mole) is added to the dimethyl sulfoxide mixture and the reaction allowed to stir at ambient temperature (23°). After stirring for 10 minutes an exothermic reaction begins to take place and an ice-bath is used to maintain the reaction temperature below 30°. After stirring for 1 hour the ice-bath is removed and the reaction allowed to stir at room temperature for 18 hours. The excess NaH is destroyed by adding 5 ml of methanol and the entire reaction mixture is then poured into 400 ml of water. The product is extracted with 3×125 ml portions of chloroform. The $CHCl_3$ extracts are combined and washed with 4×300 ml portions of water. The $CHCl_3$ layer is separated and dried over anhydrous $Na_2SO_4$ overnight. The $CHCl_3$ is then removed in vacuo yielding a pale yellow oil which is vacuum distilled through a 10 cm vigreux column and the fraction distilling at 91°-94° @ 0.4 mm is collected, yielding 4.86 g (63%) of the above compound.

D.

[[5-[[2-(Dipropylamino)-2-oxoethoxy]methyl]-tetrahydro-2-furanyl]methoxy]acetic acid Following the procedure of Example 3D, except substituting 2-[[5-[[(2,2-dimethyl-1,3-dioxolan-4-yl)methoxy]methyl]tetrahydro-2-furanyl]methoxy]-N,N-dipropylacetamide for 2-[[6-[(2-propenyloxy)methyl]-1,4-dioxan-2-yl]methoxy]acetic acid, the title product is obtained.

EXAMPLES 7 AND 8

Following the procedure of Example 1 except substituting for 1,5-hexadiene diepoxide, the diepoxide shown in Column I of Table A set out below, the novel intermediate shown in Column II is obtained.

TABLE A

| Ex. No. | X | Column I 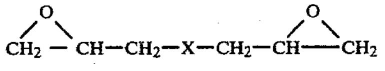 | Column II 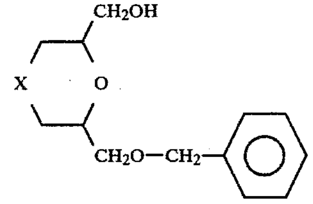 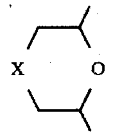 |
|---|---|---|---|
| 7. | $CH_2$ | | 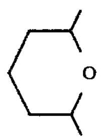 |
| 8. | O | | 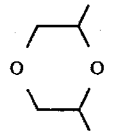 |

EXAMPLES 9 TO 19

Following the procedure of Example 1B, except substituting for tetrahydro-5-[(phenylmethoxy)methyl]-2- furanmethanol, the intermediates of Examples 1B, 7 and 8 (shown in Column I of Table B below), and substituting for 2-chloro-N,N-dipropylacetamide, the amide shown in Column II, the novel intermediate shown in Column III is obtained.

EXAMPLES 20 TO 30

Following the procedure of Example 1C, except substituting for N,N-dipropyl-2-[[tetrahydro-5-[(phenylmethoxy)methyl]-2-furanyl]methoxy]acetamide, the intermediates of Examples 9 to 19 (shown in Column I of Table C below), the novel intermediate shown in Column II is obtained.

TABLE B

| | Column I | Column II | Column III | |
|---|---|---|---|---|
| | 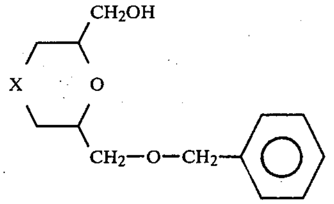 | 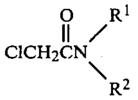 | 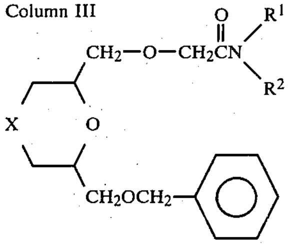 | |
| Ex. No. | X | 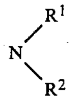 | X | 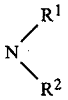 |
| 9. | — | 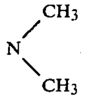 | as in Column I | as in Column II |
| 10. | —CH₂— | 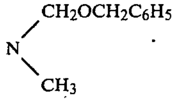 | | |
| 11. | —O— | 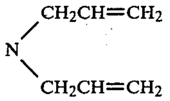 | | |
| 12. | — | 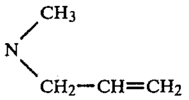 | | |
| 13. | —CH₂— | 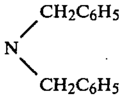 | | |
| 14. | —O— | 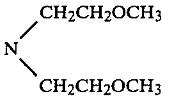 | | |
| 15. | — | 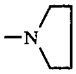 | | |
| 16. | —CH₂— | 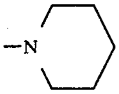 | | |
| 17. | —O— | 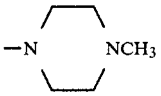 | | |
| 18. | — | 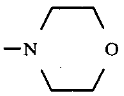 | | |
| 19. | —CH₂— | 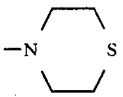 | | |

TABLE C

| | Column I | | Column II | |
|---|---|---|---|---|
| | 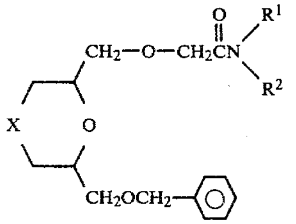 | | 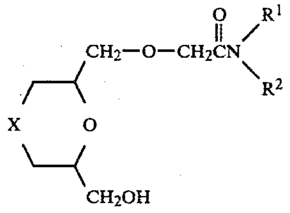 | |
| Ex. No. | X | 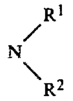 | X | 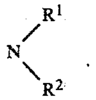 |
| 20. | — | 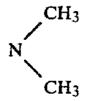 | as in Column I | as in Column II |
| 21. | $-CH_2-$ | 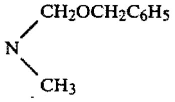 | | |
| 22. | $-O-$ | 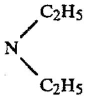 | | |
| 23. | — | 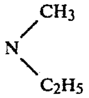 | | |
| 24. | $-CH_2-$ | 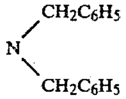 | | |
| 25. | $-O-$ | 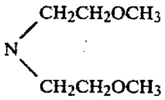 | | |
| 26. | — | 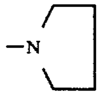 | | |
| 27. | $-CH_2-$ | 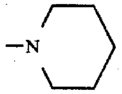 | | |
| 28. | $-O-$ | 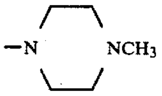 | | |
| 29. | — | 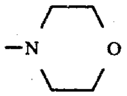 | | |
| 30. | $-CH_2-$ | 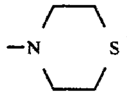 | | |

EXAMPLES 31 TO 41

Following the procedure of Example 1D, except substituting for N,N-dipropyl-2-[[tetrahydro-5-(hydroxymethyl)-2-furanyl]methoxy]acetamide, the intermediates of Examples 20 to 30 (shown in Column I of Table D below), and substituting for 2-chloro-N,N-dipropylacetamide, the amide shown in Column II, the product shown in Column III is obtained.

TABLE D
| | Column I | | Column II | Column III | | |
|---|---|---|---|---|---|---|
| | 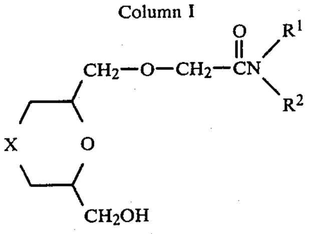 | | 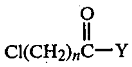 | 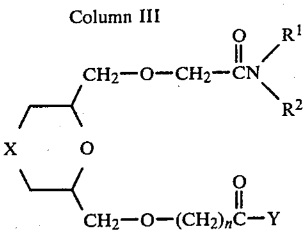 | | |
| Ex. No. | X | 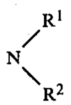 | 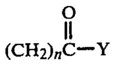 | X | 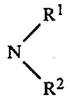 | 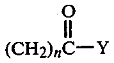 |
| | | | | as in Column I | | as in Column II |
| 31. | — | 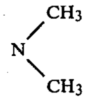 | 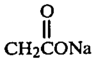 | | | |
| 32. | —CH2— | 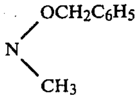 | 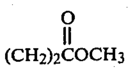 | | | |
| 33. | —O— | 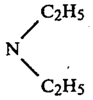 | 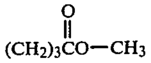 | | | |
| 34. | — | 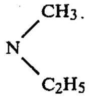 | 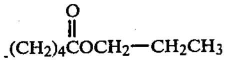 | | | |
| 35. | —CH2— | 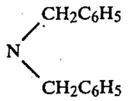 | 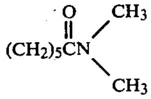 | | | |
| 36. | —O— | 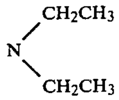 | 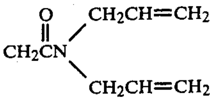 | | | |
| 37. | — | 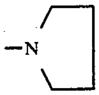 | 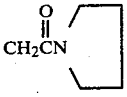 | | | |
| 38. | —CH2— | 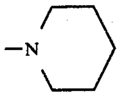 | 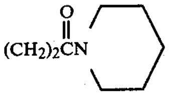 | | | |
| 39. | —O— | 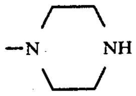 | 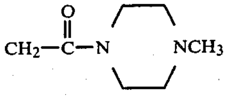 | | | |
| 40. | — | 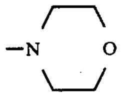 | 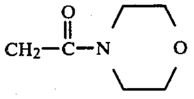 | | | |
| 41. | —CH2— | 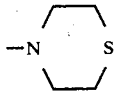 | 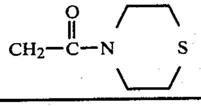 | | | |
EXAMPLES 42 AND 43
Following the procedure of Example 3B except substituting for diglycidyl ether, the epoxide shown in Column I of Table E set out below, the novel intermediate shown in Column II is obtained.

TABLE G-continued
| | | Column I 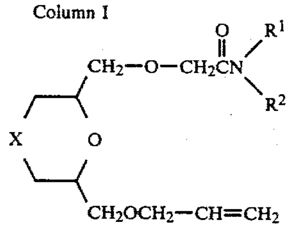 | | Column II 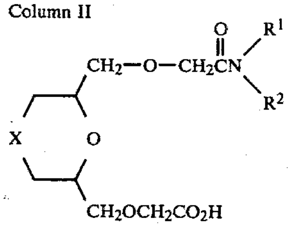 |
|---|---|---|---|---|
| Ex. No. | X | 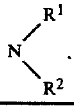 | X | 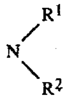 |
| 57. | —O— | 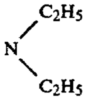 | | |
| 58. | — | 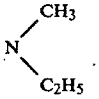 | | |
| 59. | —$CH_2$— | 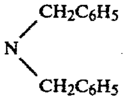 | | |
| 60. | —O— | 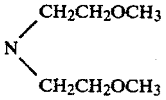 | | |
| 61. | — | 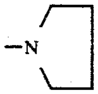 | | |
| 62. | —$CH_2$— | 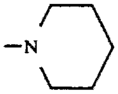 | | |
| 63. | —O— | 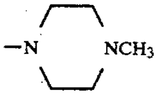 | | |
| 64. | — | 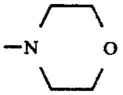 | | |
| 65. | —$CH_2$— | 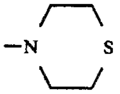 | | |
EXAMPLES 66 AND 67
Following the procedure of Example 5B, except substituting for 1,6-heptadiene diepoxide, the epoxide shown in Column I of Table H below, the novel intermediate shown in Column II is obtained.

TABLE H

| Ex. No. | Column I<br>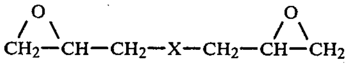<br>X | Column II<br>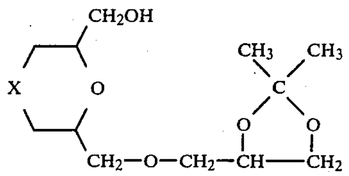<br>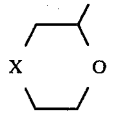 |
|---|---|---|
| 66. | $CH_2$ | 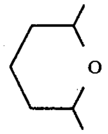 |
| 67. | O | 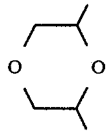 |

EXAMPLES 68 TO 78

Following the procedure of Example 5C, except substituting for 6-[[(2,2-dimethyl-1,3-dioxolan-4-yl)methoxy]methyl]tetrahydro-2H-pyran-2-methanol, the intermediates of Examples 5B, 66 and 67 (shown in Column I of Table I below), and substituting for 2-chloro-N,N-dipropylacetamide, the amide shown in Column II, the novel intermediate shown in Column III is obtained.

TABLE I

| Ex. No. | Column I<br>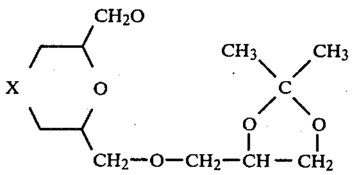<br>X | Column II<br>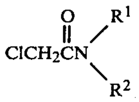<br>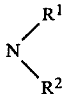 | Column III<br>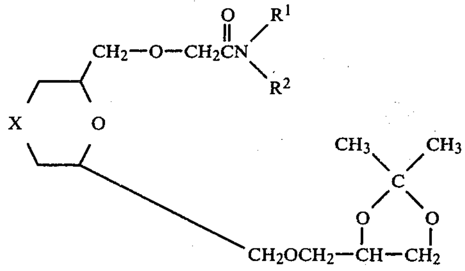<br>X | 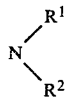 |
|---|---|---|---|---|
| 68. | — | 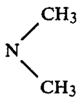 | as in Column I | as in Column II |
| 69. | $-CH_2-$ | 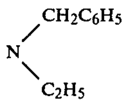 | | |
| 70. | $-O-$ | 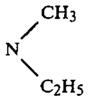 | | |
| 71. | — | 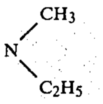 | | |

TABLE E

| | Column I | Column II |
|---|---|---|
| | 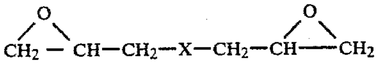 | 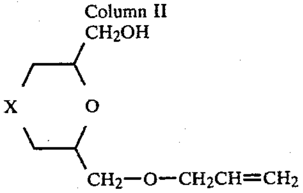 |
| Ex. No. | X | 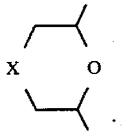 |
| 42. | $CH_2$ | 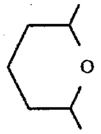 |
| 43. | — | 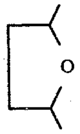 |

EXAMPLES 44 TO 54

Following the procedure of Example 3B and 3C, except substituting for 6-[(2-propenyloxy)methyl]-1,4-dioxane-2-methanol, the intermediates of Examples 3B, 42 and 43 (shown in Column I of Table F below), and substituting for 2-chloro-N,N-dipropylacetamide, the amide shown in Column II, the novel intermediate shown in Column III is obtained.

TABLE F

| | Column I | Column II | Column III | |
|---|---|---|---|---|
| | 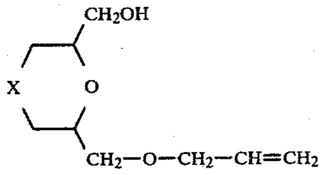 | 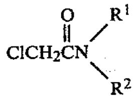 | 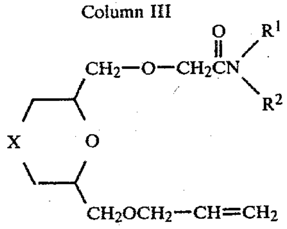 | |
| Ex. No. | X | 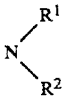 | X | 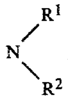 |
| 44. | — | 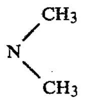 | as in Column I | as in Column II |
| 45. | $-CH_2-$ | 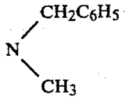 | | |
| 46. | $-O-$ | 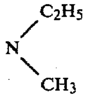 | | |
| 47. | — | 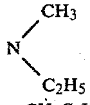 | | |
| 48. | $-CH_2-$ | 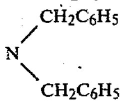 | | |

TABLE F-continued

| Ex. No. | Column I 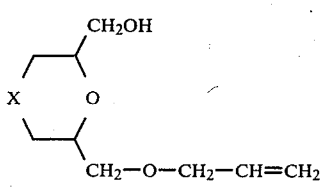 X | Column II 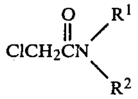 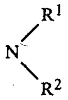 | Column III 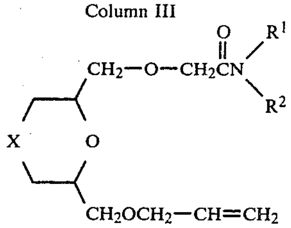 X | 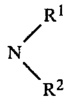 |
|---|---|---|---|---|
| 49. | —O— | 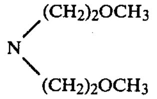 | | |
| 50. | — | 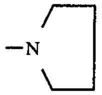 | | |
| 51. | —CH₂— | 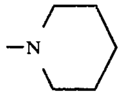 | | |
| 52. | —O— | 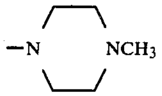 | | |
| 53. | — | 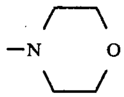 | | |
| 54. | —CH₂— | 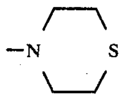 | | |

EXAMPLES 55 TO 65

Following the procedure of Example 3D, except substituting for 2-[[6-[(2-propenyloxy)methyl]-1,4-dioxan-2-yl]methoxy]-N,N-dipropylacetamide, the intermediates of Examples 44 to 54 (shown in Column I of Table G below), the novel products shown in Column II are obtained.

TABLE G

| Ex. No. | Column I 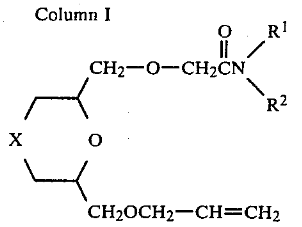 X | 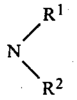 | Column II 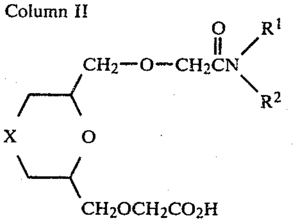 X | 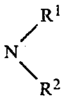 |
|---|---|---|---|---|
| 55. | — | 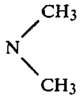 | as in Column I | as in Column II |
| 56. | —$CH_2$— | 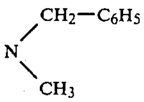 | | |

TABLE I-continued

| | Column I | Column II | | Column III |
| --- | --- | --- | --- | --- |
| | 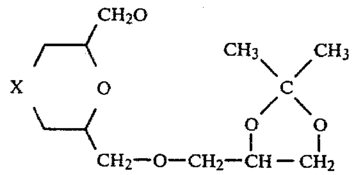 | 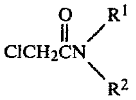 | | 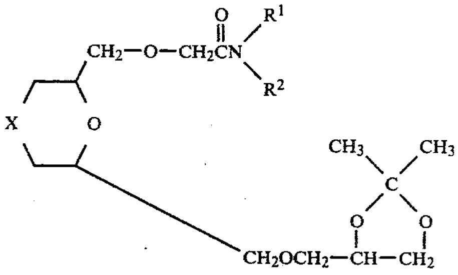 |
| Ex. No. | X | 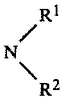 | X | 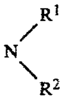 |
| 72. | $-CH_2-$ | 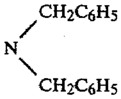 | | |
| 73. | $-O-$ | 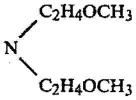 | | |
| 74. | — | 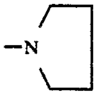 | | |
| 75. | $-CH_2-$ | 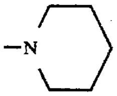 | | |
| 76. | $-O-$ | 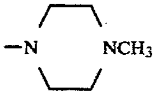 | | |
| 77. | — | 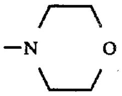 | | |
| 78. | $-CH_2-$ | 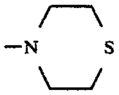 | | |

EXAMPLES 79 TO 89

Following the procedure of Example 5D, except substituting for [[6-[[(2,2-dimethyl-1,3-dioxolan-4-yl)methoxy]methyl]tetrahydro-2H-pyran-2-yl]methoxy]-N,N-dipropylacetamide, the intermediates of Examples 68 to 78 (shown in Column II of Table I), the novel products of Examples 55 to 65 shown in Column II of Table G are obtained.

What is claimed is:

1. A compound having the structure

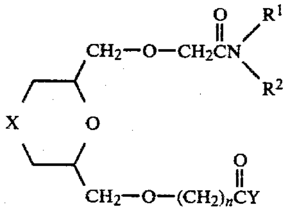

wherein X is a single bond, $-CH_2-$ or $-O-$, $R^1$ and $R^2$ may be the same or different and are lower akyl, lower alkenyl, phenyl lower alkyl, phenyl-lower alkoxy-lower alkyl, or lower alkoxy or

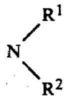

may be taken together to form a 5- to 7-membered saturated heterocyclic ring optionally containing one other hetero atom, which is nitrogen, oxygen, or sulfur, Y is hydroxyl, OR or

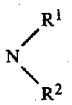

wherein R is lower alkyl, lower alkenyl, or lower alkanoyl and $R^1$, $R^2$ and

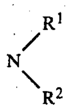

are as defined above, with the proviso that where both

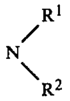

and Y are heterocycles, they are the same heterocycle, and n is an integer from 1 to 6, and when Y=OH, pharmaceutically acceptable base addition salts thereof.

2. The compound of claim 1 wherein X is a single bond.

3. The compound of claim 1 wherein X is —O—.

4. The compound of claim 1 wherein X is $—CH_2—$.

5. The compound of claim 1 wherein $R^1$ and $R^2$ are each lower alkyl.

6. The compound of claim 1 wherein n is 1 or 2 and Y is

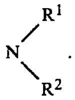

7. The compound of claim 4 wherein Y is di(lower alkyl)amino.

8. The compound of claim 5 wherein X is a single bond, $R^1$ and $R^2$ are each lower alkyl, n is 1 and Y is di(lower alkyl)amino.

9. The compound of claim 8 having the name 2,2'-[tetrahydrofuran-2,5-diylbis(methoxy)]bis[N,N-dipropylacetamide].

10. A pharmaceutical composition for use in treating arrhythmia comprising an anti-arrhythmia effective amount of a compound as defined in claim 1 and a pharmaceutically acceptable carrier therefor.

11. A method for treating arrhythmia in mammals which comprises administering to a mammalian host an anti-arrhythmia effective amount of a compound as defined in claim 1.

* * * * *

UNITED STATES PATENT AND TRADEMARK OFFICE

CERTIFICATE OF CORRECTION

PATENT NO. : 4,279,902

DATED : July 21, 1981

INVENTOR(S) : Frederic P. Hauck et al.

It is certified that error appears in the above-identified patent and that said Letters Patent are hereby corrected as shown below:

Column 2, line 50, "8 e.g." should read -- [e.g. --.
Column 3, line 67, "ration" should read --ratio--.
Column 8, line 37, "whih" should read --which--.
Columns 27 and 29, TABLE 1, Column 1, the structure in the heading should read -- 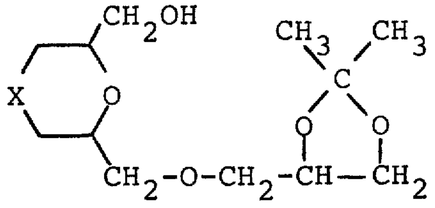 --.

Signed and Sealed this

Thirteenth Day of October 1981

[SEAL]

Attest:

GERALD J. MOSSINGHOFF

Attesting Officer

Commissioner of Patents and Trademarks